United States Patent [19]

Winkelmann et al.

[11] 3,962,454

[45] June 8, 1976

[54] BIS-(1-ALKYL-5-NITRO-IMIDAZOLYL-2-ALKYL)-COMPOUNDS

[75] Inventors: Erhardt Winkelmann, Kelkheim, Taunus; Wolfgang Baether, Dreieichenhain, both of Germany

[73] Assignee: Hoechst Aktiengesellschaft, Frankfurt am Main, Germany

[22] Filed: Feb. 19, 1975

[21] Appl. No.: 550,919

[30] Foreign Application Priority Data

Feb. 21, 1974 Germany............................ 2408219

[52] U.S. Cl................................ 424/273; 260/309
[51] Int. Cl.²....................................... C07D 233/94
[58] Field of Search.................... 260/309; 424/273

[56] References Cited
OTHER PUBLICATIONS

Kochergin et al. Chem. Abst. 1967, vol. 66, No. 104955u.
Schubert et al. Chem. Abst. 1968, vol. 68, No. 95760p.
Sunjic et al. Chem. Abst. 1970, vol. 72, No. 66866e.

*Primary Examiner*—Natalie Trousof
*Attorney, Agent, or Firm*—Curtis, Morris & Safford

[57] ABSTRACT

Bis-(1-alkyl-5-nitro-imidazolyl)-compounds as well as a process for their manufacture are described. The compounds are active against protozoal diseases.

6 Claims, No Drawings

BIS-(1-ALKYL-5-NITRO-IMIDAZOLYL-2-ALKYL)-COMPOUNDS

The present invention relates to bis-(1-alkyl-5-nitroimidazolyl-2-alkyl) compounds and to a process for their manufacture.

It is known to use 1-(2-hydroxyethyl)-2-methyl-5-nitroimidazole (Metronidazol) for the treatment of protozoal diseases such as trichomoniasis and amebiasis.

This invention relates to bis-(1-alkyl-5-nitroimidazolyl2-alkyl)-sulfides, sulfoxides, sulfones as well as disulfides of the formula I

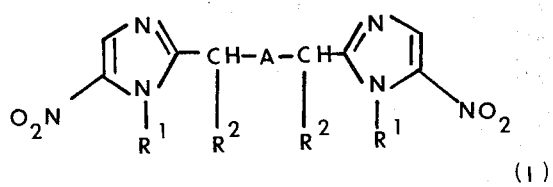

wherein $R^1$ stands for a methyl or ethyl group, $R^2$ is a hydrogen atom or a methyl group, A a sulfur bridge (—S—), a sulfoxide group (—SO—), a sulfone group (—SO$_2$) or a disulfide bridge (—S—S—).

The novel compounds are effective against various protozoa, in particular trichomonads and amebae, and, also, trypanosoma and bacteria.

This invention further relates to a process for the manufacture of bis-(1-alkyl-5-nitro-imidazolyl-2-alkyl)-sulfides, sulfoxides and sulfones or disulfides of the formula I, which comprises a. reacting a 1-alkyl-2-halogenalkyl-5-nitro-imidazole of the formula II

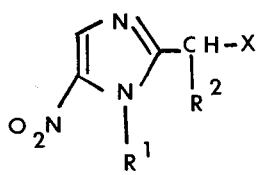

wherein $R^1$ and $R^2$ have the meanings indicated in formula I and X is halogen or an acyloxy group, preferably acetoxy, propionyloxy, butyryloxy, benzoyloxy or phenylacetoxy, or an arylsulfonic acid ester group, preferably a benzenesulfonic acid ester group, toluenesulfonic acid ester or napthalenesulfonic acid ester group, with hydrogen sulfide or the alkali metal or ammonium salt thereof having the formula III $$Y - S - Y \qquad (III)$$

wherein Y is hydrogen, an alkali metal, especially sodium or potassium, or ammonium, or reacting b. 1-alkyl-2-mercaptoalkyl-5-nitro-imidazole of the formula IV

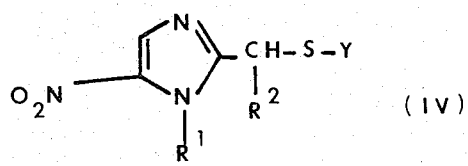

wherein $R^1$, $R^2$ and Y have the above meanings, with a 1-alkyl-2-halogenalkyl-5-nitro-imidazole of the formula II and, optionally, oxidizing the sulfide compound of the formula I to a sulfoxide or sulfone, or c. reacting 1-alkyl-2-halogenalkyl-5-nitro-imidazole of the formula II

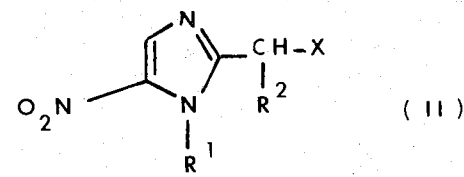

wherein $R^1$ and $R^2$ have the meanings mentioned in formula I and X is halogen or acyloxy, preferably acetoxy, propionyloxy, butyryloxy, benzoyloxy or phenylacetoxy, or an arylsulfonic acid ester group, preferably a benzenesulfonic acid ester group, toluenesulfonic acid ester or naphthalene-sulfonic acid ester group, with a dialkali disulfide of the formula V $$Y' - S - S - Y' \qquad (V)$$

wherein Y' is an alkali metal, especially sodium or potassium, or ammonium, or d. oxidizing 1-alkyl-2-mercaptoalkyl-5-nitro-imidazole of the formula IV

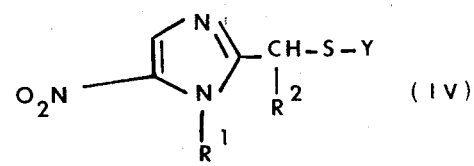

wherein $R^1$, $R^2$ and Y have the above meanings.

According to the processes a) and b) there are formed the sulfides, sulfoxides and sulfones, according to the processes c) and d) the disulfides of the formula I.

Some examples of the compounds of formula II which may be used as starting materials are 1-methyl-2-chloro-methyl-5-nitro-imidazole, 1-methyl-2-bromo-methyl-5-nitro-imidazole, 1-methyl-2-iodo-methyl-5-nitro-imidazole, 1-ethyl-2-chloro-methyl-5-nitro-imidazole, 1-ethyl-2-bromo-methyl-5-nitro-imidazole, 1-ethyl-2-iodo-methyl-5-nitro-imidazole, 1-methyl-2-chloro-(1-ethyl)-5-nitro-imidazole, 1-methyl-2-bromo-(1-ethyl)-5-nitro-imidazole, 1-methyl-2-iodo-(1-ethyl)-

5-nitro-imidazole, 1-ethyl-2-chloro-(1-ethyl)-5-nitro-imidazole, 1-ethyl-2-bromo-(1-ethyl)-5-nitro-imidazole, 1-ethyl-2-iodo-(1-ethyl)-5-nitro-imidazole, 1-methyl-2-acetoxy-methyl-5-nitro-imidazole, 1-ethyl-2-acetoxy-methyl-5-nitro-imidazole, 1-methyl-2-benzoyloxymethyl-5-nitro-imidazole, 1-ethyl-2-benzoyloxymethyl-5-nitro-imidazole, 1-ethyl-2-benzoyloxymethyl-5-nitro-imidazole, 1-methyl-2-benzene-sulfonyloxymethyl-5-nitro-imidazole, 1-ethyl-2-benzene-sulfonyloxymethyl-5-nitro-imidazole, 1-methyl-2-toluene-sulfonyloxymethyl-5-nitro-imidazole and 1-ethyl-2-toluene-sulfonyloxymethyl-5-nitro-imidazole.

As starting products of the formula II, there may be used for example sodium, potassium and ammonium hydrogen sulfide, and sodium, potassium and ammonium sulfide.

Some examples of the compounds of formula IV which may be used as starting materials are 1-methyl-2-mercapto-methyl-5-nitro-imidazole, 1-ethyl-2-mercapto-methyl-5-nitro-imidazole, 1-methyl-2-mercapto-(1-ethyl)-5-nitro-imidazole and 1-ethyl-2-mercapto-(1-ethyl)-5-nitro-imidazole or the alkali metal or ammonium salts thereof, or mercaptane-yielding substances, such as isothiouronium salts, isothioamide compounds, xanthogenates, thiosulfates, thioacetates, thiobenzoates, thiocarbamates, dithiocarbamates, thiocyanates.

As starting substances of the formula V there may be used for example disodium, dipotassium and diammonium disulfide.

The 1-alkyl-2-chloroalkyl-nitro-imidazoles of the formula II used as starting compounds are obtained by reacting 1-alkyl-2-hydroxyalkyl-5-nitroimidazoles with thionyl chloride, which may be optionally converted into the corresponding fluorinated, brominated or iodinated compounds by reaction with other metal halides.

The 1-alkyl-2-acyloxy-alkyl-5-nitro-imidazoles or 1-alkyl-2-(arylsulfonyloxyalkyl)-5-nitro-imidazoles of the formula II used as starting compounds are obtained by reacting corresponding 1-alkyl-2-hydroxyalkyl-5-nitro-imidazoles with an acid anhydride or acid chloride such as acetanhydride or acetyl chloride or with an arylsulfonic acid chloride such as toluene-sulfonic acid chloride.

The 1-alkyl-2-mercapto-alkyl-5-nitroimidazoles of the formula IV may be obtained from corresponding 2-halogen-alkyl-5-nitroimidazoles by reacting with hydrogen sulfide.

Due to the instability, i.e. the easy oxidizability, it is recommandable, however, to react the alkalizers or the corresponding mercaptane-yielding agents.

The variants a), b) and c) of the process of the invention are advantageously carried out using equimolar amounts of each starting substance, preferably in a solvent or dispersing agent. When using the compounds of the formula III or IV the solvent used is preferably a polar one; when using the salts thereof, the solvent chosen is preferably a non polar one.

As non polar solvents there are mentioned, for example, benzene, toluene, xylene, chlorobenzene. As polar solvents there are mentioned, for example, alcohols such as methanol, ethanol, propanol, butanol, methoxyethanol or ketones such as acetone, methylethyl-ketone, methylbutyl-ketone, further pyridine, picoline, quinoline, dimethylformamide, dimethylacetamide, N-methylpyrrolidone, tetra-methyl-urea, hexamethylphosphoric acid triamide or dimethylsulfoxide.

The reaction temperatures may generally be in the range of from 0° to 120°C, preferably between 15° and 60°C. In this connection the reactions using polar solvents may be carried out at lower temperatures, those using non-polar solvents suitably at elevated temperatures. Depending on the temperatures chosen, the reaction times range from a few minutes to several hours.

If the compounds of the formula II and IV are used, it is advisable to use an acid-binding agent. As agents of this kind use may be made of bases such triethyl amide or pyridine, as well as alkali metal and alkaline earth metal carbonates and bicarbonates, hydroxides and alkoxides, for example methoxides, ethoxides and butoxides.

The products of the process are isolated according to usual methods by distilling off the solvents used or by diluting the reaction solution with water. Optionally the products of the invention may be purified by a recrystallization from an appropriate solvent mixture.

The sulfides of the formula I (A = —S—) obtained according to one of the above-mentioned process variants a) or b) may be converted by oxidation into the corresponding sulfoxides (A = —SO—) or sulfones (A = —SO$_2$—).

The oxidation reactions are advantageously carried out using simple or double molar amounts of an oxidizing agent. By the treatment of the sulfides with one mol-equivalent of the oxidizing agent, sulfoxides are obtained and with two mol-equivalents of the oxidizing agent sulfones are obtained. As oxidizing agents, there may be used, for example, hydrogen peroxide or peroxy acids such as, for example, peracetic acid, petrifluoro-acetic acid or metachloro-perbenzoic acid as well as nitric acid or chromic acid, or the salts thereof, furthermore permanganates, hypochlorites, perchlorates, periodates and nitrogen oxides. The oxidation reactions are advantageously carried out in a solvent or dispersing agent.

For this purpose, those solvents are particularly useful which are not attacked by the oxidizing agent, for example acetic acid or trifluoro-acetic acid. When perbenzoic acid is used, methylene chloride or chloroform are also useful as solvents.

The oxidation reactions which are optionally carried out after the processes a) and b) and yield sulfoxides are generally carried out at temperatures ranging from 10° to 30°C. The sulfones are generally obtained at oxidation temperatures of from 50° to 100°C. The sulfones may also be prepared by oxidation of the corresponding sulfoxides by means of the above-specified oxidizing agents at elevated temperatures.

Depending on the temperature chosen and on the desired final product, the oxidation times range from a few minutes to several hours.

The variant d) of the process of the invention is expediently carried out with equimolar amounts of a mild oxidizing agent. As oxidizing agents there may be used for example: Hypohalides, halogens such as iodine, dirhodane, iron(III)-chloride, potassium-hexacyano-ferrate-III, oxygen, air, hydrogen peroxide or oxygen-yielding compounds as for example dimethylsulfoxide.

As solvent or diluent there are suitable for example water, glacial acetic acid, methylene chloride, chloroform. The oxidation temperatures expediently range between 0° and 30°C.

The products of the invention are isolated by diluting the reaction solution with water and, at the same time, precipitating them, or by evaporating the organic solvent under reduced pressure. They may be purified, where required, by recrystallizing them from a suitable solvent or mixture of solvents.

The novel compounds of the formula I are well compatible and are effective against pathogens, such as bacteria and protozoa. They are especially active against trichomonads and amebae and are in this respect superior to the known Metronidazole.

The novel compounds of formula I are therefore suitable for the treatment of protozoal diseases in human beings and animals, as they are caused, for example, by infections with Trichomonas vaginalis and Entamoeba histolytica, as well as with trypanosoma cruci, trypanosoma brucei and trypanosoma congolense.

The novel compounds of the formula I can be administered orally or locally.

The dosage unit for oral administration is given in the form of tablets or capsules containing, per daily dosage unit, about 10 to 750 mg, preferably 150 to 500 mg, of the active substance in combination with a pharmaceutically acceptable carrier and/or diluent. For local application, for example, jellies, creams, ointments or suppositories are useful. For oral administration for animals usual feeding stuff is considered as carrier.

The individual dosage units of the novel compounds of formula I are expediently between 5 and 100 mg per kg of body weight.

EXAMPLES OF PREPARATION

1. Bis-(1-methyl-5-nitro-imidazolyl-2-methyl)-sulfide 35.10 g (0.2 mol) of 1-methyl-2-chloromethyl-5-nitro-imidazole were dissolved in 250 ml of ethanol, and at 20°C, while stirring well and cooling with ice, a solution of 24.0 g (0.1 mol) of sodium sulfide nonahydrate in 75 ml of water and 75 ml of ethanol were added dropwise within about 30 minutes. After the end of the exothermic reaction stirring was continued for one hour at room temperature. By dropwise addition of 200 ml of water the beginning crystallization was completed, the crude crystallized product was suction-filtered and recrystallized from ethanol with addition of charcoal.

Thus, 23.5 g (corresponding to 75.3 percent of the theory) of bis-(1-methyl-5-nitro-imidazolyl-2-methyl)-sulfide were obtained in the form of yellowish crystals having a melting point of 135°C.

In the same manner the following compounds were obtained:

2. Bis-(1-ethyl-5-nitro-imidazolyl-2-methyl)-sulfide, melting point 90°C, from 1-ethyl-2-chloromethyl-5-nitro-imidazole and sodium sulfide.

3. Bis-[1-methyl-5-nitro-imidazolyl-2-(1-ethyl)]-sulfide, melting point 85°C from 1-methyl-2-(1-chloroethyl)-5-nitro-imidazole and sodium sulfide.

Bis-(1-methyl-5-nitro-imidazolyl-2-methyl)-sulfide was also obtained by the reaction of 1-methyl-2-chloromethyl-5-nitro-imidazole with sodium hydrogensulfide monohydrate in ethanol at 0° to 10°C or by reaction of 1-methyl-2-chloro-methyl-5-nitro-imidazole with thioacetamide or thio-urea in dimethylacetamide in the presence of potassium carbonate at 80°C, without isolating the isothio-uronium or isothio-acetamide intermediate compound (mercaptane-yielding agent).

4. Bis-(1-methyl-5-nitro-imidazolyl-2-methyl)-sulfoxide 31.2 g (0.1 mol) of bis-(1-methyl-5-nitro-imidazolyl-2-methyl)-sulfide were dissolved in 300 ml of chloroform, and while stirring, 17.25 g (0.1 mol) of m-chloroperbenzoic acid dissolved in 50 ml of chloroform were added dropwise at room temperature. The reaction solution was then stirred for another hour at room temperature, extracted with diluted soda solution, the chloroform phase was separated, dried over sodium sulfate and evaporated. The residue was recrystallized from alcohol.

Thus, 21.6 g of bis-(1-methyl-5-nitro-imidazolyl-2-methyl)-sulfoxide (corresponding to 66 percent of the theory) were obtained in the form of yellowish crystals having a melting point of 162°C.

In the same manner the following compounds was obtained in good yeild:

5. Bis-(1-ethyl-5-nitro-imidazolyl-2-methyl)-sulfoxide, melting point 116°C, by oxidation of bis-(1-ethyl-5-nitro-imidazolyl-2-methyl)-sulfide.

6. Bis-(1-methyl-5-nitro-imidazolyl-2-methyl)-sulfone 31.2 g (0.1 mol) of bis-(1-methyl-5-nitro-imidazolyl-2-methyl)-sulfide were dissolved in 500 ml of glacial acetic acid and while stirring, 20.0 ml (0.2 mol) of a 35 percent hydrogen peroxide were added dropwise at room temperature. Then the mixture was stirred for two hours while heating to 70°–80°C. The reaction solution was evaporated under reduced pressure and the residue was recrystallized from water/alcohol. Thus, 26.8 g of bis-(1-methyl-5-nitro-imidazolyl-2-methyl)-sulfone (corresponding to 78 percent of the theory) were obtained in the form of yellowish crystals having a melting point of 185°C.

In the same manner the following compound was obtained in good yield:

7. Bis-(1-ethyl-5-nitro-imidazolyl-2-methyl)-sulfone, melting point 138°C, by oxidation of bis-(1-ethyl-5-nitro-imidazolyl-2-methyl)-sulfide.

8. Bis-(1-methyl-5-nitro-imidazolyl-2-methyl)-disulfide 35.10 g (0.2 mol) of 1-methyl-2-chloromethyl-5-nitro-imidazole were dissolved in 100 ml of dimethyl sulfoxide and at 10° – 20°C, a solution of 7.2 g (0.1 mol) of potassium hydrogen sulfide (freshly prepared by introducing hydrogen sulfide into concentrated aqueous potassium hydroxide solution and evaporating in vacuo) in 70 ml of dimethyl sulfoxide were added dropwise, while stirring well. Then the solution turning to dark red was stirred for one hour at room temperature, and while stirring, water was added dropwise until crystalline separation. The crude product was suction-filtered and recrystallized from ethanol/dimethylformamide and then from butanol with addition of charcoal.

Thus, 17.9 g (corresponding to 52 percent of the theory) of bis-(1-methyl-5-nitro-imidazolyl-2-methyl)-disulfide were obtained in the form of light yellow crystals having a melting point of 193°C with decomposition.

In the same way there was obtained the following compounds:

9. Bis-(1-ethyl-5-nitro-imidazolyl-2-methyl)-disulfide, melting point 154°C, from 1-ethyl-2-chloromethyl-5-nitro-imidazole and potassium hydrogen sulfide in the presence of di-methyl sulfoxide as solvent and oxidating agent.

Bis-(1-methyl-5-nitro-imidazolyl-2-methyl)-disulfide was also obtained by the reaction of 1-methyl-2-chloromethyl-5-nitro-imidazole with disodium disulfide in ethanol or by the reaction of 1-methyl-2-chloromethyl-5-nitro-imidazole with potassium rhodanide in dimethyl sulfoxide at room temperature (without isolating the thiocyanate intermediate compound) and subsequent action of a strong base such as for example tri-ethanol amine or sodium hydroxide solution at room temperature, or heating the thiocyanate intermediate compound in a dimethylsulfoxide solution to 150°C.

PROCESS B

EXAMPLE 10

By the reaction of 25.2 g (0.1 mol) of 1-methyl-2-(S-isothiouronium-methyl)-5-nitro-imidazol hydrochloride with 17.6 g (0.1 mol) of 1-methyl-2-chloromethyl-5-nitro-imidazole in 250 ml of dimethylformamide in the presence of 10.8 g (0.2 mol) of sodium methylate, during one hour at 35° – 40°C, 68 percent of the theory of bis-(1-methyl-5-nitro-imidazolyl-2-methyl)-sulfide having a melting point of 135°C were obtained.

What we claim is:

1. A bis-(1-alkyl-5-nitro-imidazolyl-2-alkyl)-sulfide, -sulfoxide, -sulfone or -disulfide of the formula

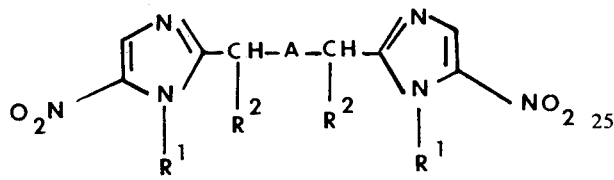

wherein $R^1$ is methyl or ethyl, $R^2$ is hydrogen or methyl and A is sulfur (-S-), sulfoxide (—SO—), sulfone (-SO$_2$) or disulfide (—S—S—).

2. A compound as defined in claim 1, which is bis-(1-methyl-5-nitro-imidazolyl-2-methyl)-sulfide.

3. A compound as defined in claim 1, which is bis-(1-methyl-5-nitro-imidazolyl-2-methyl)-sulfone.

4. A compound as defined in claim 1, which is bis-(1-methyl-5-nitro-imidazolyl-2-methyl)-disulfide.

5. A pharmaceutical composition for combating protozoal diseases caused by trichomonads, amoebae and trypanosomes containing as the active ingredient from 10 to 750 mg. per daily dosage unit of a compound defined in claim 1, in combination with a pharmaceutically acceptable carrier or with feed stuff.

6. A method of combating protozoal diseases caused by trichomonads, amoebae and trypanosomes which comprises administering to the infected organism an effective amount of a compound defined in claim 1.

* * * * *